(12) United States Patent
Wyrwa et al.

(10) Patent No.: US 6,358,967 B1
(45) Date of Patent: Mar. 19, 2002

(54) ERGOLINE AMINE DERIVATIVES WITH BLOOD PRESSURE LOWERING EFFECT

(75) Inventors: Ralf Wyrwa, Oelknitz; Albert Haertl, Jena; Erika Glusa, Erfurt; Susanne Grabley, Kelkheim; Ralf Thiericke, Jena, all of (DE)

(73) Assignee: CyBio Screening GmbH, Jena (DE)

( * ) Notice: Subject to any disclaimer, the term of this patent is extended or adjusted under 35 U.S.C. 154(b) by 0 days.

(21) Appl. No.: 09/743,869

(22) PCT Filed: Jul. 15, 1999

(86) PCT No.: PCT/DE99/02194

§ 371 Date: Apr. 19, 2001

§ 102(e) Date: Apr. 19, 2001

(87) PCT Pub. No.: WO00/04018

PCT Pub. Date: Jan. 27, 2000

(30) Foreign Application Priority Data

Jul. 17, 1998 (DE) .......................... 198 32 191

(51) Int. Cl.[7] ..................... A61K 31/48; C07D 457/02
(52) U.S. Cl. .................. 514/288; 546/67; 544/361; 540/575; 514/218; 514/253
(58) Field of Search ................. 514/288, 253, 514/218; 546/67; 544/361; 540/575

(56) References Cited

U.S. PATENT DOCUMENTS 4,500,712 A * 2/1985 Bernardi et al. .............. 546/67

* cited by examiner

Primary Examiner—Charanjit S. Aulakh
(74) Attorney, Agent, or Firm—Reed Smith LLP

(57) ABSTRACT

The invention relates to novel derivatives of ergoline of the general formula 1 in which $R^1$ together with the two adjacent N atoms is the residue of a diamine and $R^4$ together with the two adjacent carbonyl groups is the residue of a dicarboxylic acid. $R^2$, $R^3$, $R^6$, $R^7$, $R^8$ can be H or an organic radical. $R^7$ and $R^8$ are H or together are a bond.

The compounds show a strong antihypertensive effect. These effects moreover occur after intravenous and enteral administration even at dosages in the region of a few μg/kg (body weight). The compounds can accordingly be used as pharmaceuticals for hypertensive diseases in human medicine.

10 Claims, 1 Drawing Sheet

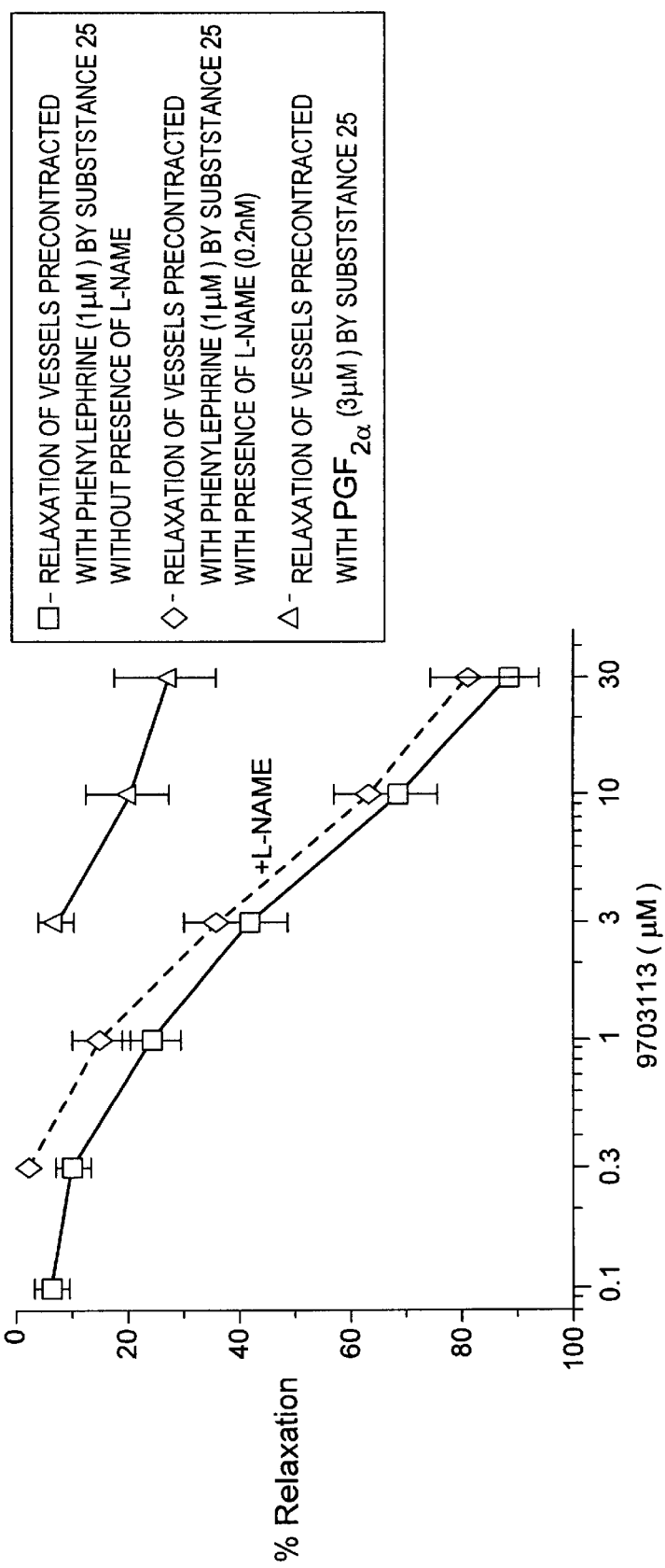

ERGOLINE AMINE DERIVATIVES WITH BLOOD PRESSURE LOWERING EFFECT

This application is a 371 of PCT/DE99/02194 filed Jul. 15, 1999, now WO 00/04018 Jan. 27, 2000.

The invention relates to novel ergoline amine derivatives with an antihypertensive effect, in particular for use in medicine.

About 10 million people in Germany alone suffer from high blood pressure [E. König, Bluthochdruck, Erste Warnsignale, Gefahren und Behandlung, Wort & Bild Verlag Konradshöhe, GmbH & Co. Baierbrunn, 1995]. There is still a pressing need for novel agents with novel principles of action, in particular without the unwanted side effects frequently occurring with the known products, for treating this disease, which is regarded as a major risk factor for various cardiovascular disorders such as arteriosclerosis, myocardial infarction, stroke and kidney damage.

The ergoline amine derivatives previously disclosed and described in the literature mainly have antisecretory and antiulcer effects. Also known from this class of substances are stimulators of the central nervous system and ergoline thiourea derivatives with antiparkinson activity. Other ergoline derivatives show antiprolactin activity, serotonin antagonistic effects, sympatholytic and oxytocin-like activity. In the search for novel antihypertensives, among the ergot alkaloids which mostly have pressor activity also a few 8β-aminomethylergoline derivatives with an antihypertensive effect have been found, with urea and thiourea derivatives [A. Temperilli, D. Ruggieri, P. Salvati, *Eur. J. Med. Chem.*, 1988, 23, 77.] or organometallic derivatives of 8β-aminomethylergoline acting as structural elements. It is known that a number of unwanted side effects occur after use of antihypertensives such as, for example, clonidine, reserpine, nifedipine, dihydralazine, and known urea and thiourea derivatives of 8β-aminomethylergoline, especially nausea, diarrhea, fatigue, depression and edema.

Overall, it is estimated that known drugs with antihypertensive activity do not meet the requirements for adequate hypotensive activity and good tolerability, which makes it necessary to look for novel compounds, especially with novel mechanisms of action.

The invention is based on the object of providing suitable, readily soluble, selectively acting and well tolerated drugs which have high antihypertensive activity after enteral and parenteral administration. The compounds are intended to make effective treatment of hypertensive diseases possible and to be better tolerated than therapeutic agents used to date.

The object is achieved according to the invention by providing novel 8β-aminomethylergoline derivatives which comprise a diamine structural unit coupled via a dicarboxylic acid. It has been found, surprisingly, that 8β-aminomethylergoline derivatives which are linked via the aminomethyl group by means of a dicarboxylic acid to a diamine have a pronounced antihypertensive effect, with both the extent of the lowering of blood pressure and the duration of the pharmacological effect being controlled via the diamine/dicarboxylic acid combination, structure-activity relations being derivable. Novel principles of action arise from the molecular structures of the introduced side chain, which differs greatly from conventional peptides.

The tested compounds show on intravenous and enteral (intraduodenal) administration of 0.1 to 5 mg/kg of body weight to anesthetized rats a dose-dependent and persistent, large hypotensive effect and show on isolated vessels a high selectivity on the $\alpha_1$ receptor.

The hypotensive effect of the compounds of the invention is not caused by an effect on the central nervous system.

Substances in therapeutic use, such as minoxidil and dihydroergocornine, are exceeded in their effect many times by the substances of the invention. The unwanted side effects frequently observed with lysergic acid derivatives can be avoided by very much lower active doses.

The aminoergoline derivatives of the invention have the general formula 1:

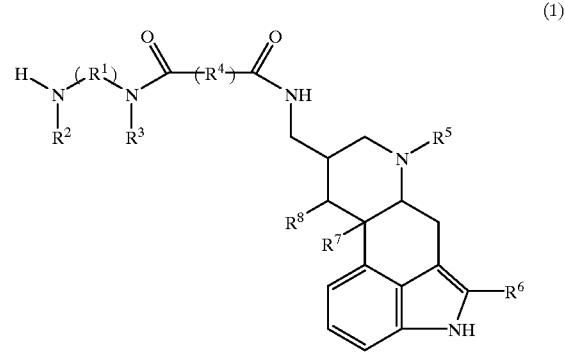

in which
 $R^5$=H, alkyl, aryl, acyl, CN;
 $R^6$=H, alkyl, halogen;
 $R^7$, $R^8$=H or together a bond;
 $R^1$ together with the two adjacent N atoms is the residue of a diamine,
 $R^4$ together with the two adjacent carbonyl groups is the residue of a dicarboxylic acid,
 $R^2$ is H, acyl and $R^3$ is H, or
 $R^2$ and $R^3$ together are a divalent radical $R^1$, and salts, in particular pharmaceutically usable salts, of these compounds.
 $R^1$ and $R^4$ have the following meanings in particular:
 a) $R^1$ and $R^4$ are, independently of one another, $C_1$–$C_{10}$-alkylene, branched or unbranched, which is optionally interrupted by O, S, $NR^9$, arylene, heteroarylene, cycloalkylene, heterocycloalkylene and/or optionally substituted by $R^{10}$,
  $R^9$=alkyl, benzyl, aryl, acyl,
  $R^{10}$=$R^9$, also halogen, OH, SH, $NO_2$, CN;
 b) $R^1$ and $R^4$ are, independently of one another, $C_1$–$C_{10}$-alkylene, branched or unbranched, which comprises one or more isolated and conjugated double bonds and is optionally substituted by $R^{10}$, and/or is optionally interrupted by O, S, NH, $NR^9$, arylene, heteroarylene, cycloalkylene, heterocycloalkylene;
 c) $R^1$ and $R^4$ are, independently of one another, cycloalkylene or heterocycloalkylene with 3–8 ring members or such cycles with, optionally, 1–2 bridges with in each case 1–3 chain members, which comprise C, O, NH, $NR^9$, S, and arylene or heteroarylene with 5–7 ring members, which are optionally substituted by $R^{10}$;
 d) $R^1$ and $R^4$ are, independently of one another, two cycloalkylenes linked by $R^{11}$ and optionally interrupted in the ring by O, S, NH, $NR^9$ and/or optionally substituted by $R^{10}$, O or S;
  $R^{11}$ alkylene, O, S, $S_2$, $NR^9$.
 $R^4$ can moreover have the following meanings:
 a) $R^4$ is two arylene or heteroarylene radicals linked by $R^{12}$;

$R^{12}$=alkylene, Fe, O, S, $S_2$, $NR^9$ b) $R^4$ is porphyrindiyl, optionally substituted one or more times by alkyl, unsaturated one or more times, having central atoms such as, for example, Zn, Ca, Mg and Fe, where a residual charge occurring after the complexation is neutralized by an anion of a pharmaceutically acceptable acid.

Salts of compounds of the formula 1 are, in particular, pharmaceutically acceptable salts and may have been produced by quaternization, either by reacting the product with conventional alkylating agents or by using building blocks which have already been quaternized. Salts of the invention are also those produced by protonation of compounds of the formula 1 by reaction with monobasic to tribasic acids with a maximum charge corresponding to the number of protonatable positions, in most cases the number of implemented nitrogen atoms. Acids which can be used in this connection are inorganic acids such as, for example, hydrohalic acids, sulfuric acid and phosphoric acid, and the amides thereof, or other pharmacologically suitable derivatives. The organic acids may be, for example, carboxylic, sulfo or sulfonic acids such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid.

Preference is given to the following compounds of the formula 1, in which $R^2$, $R^3$, $R^6$, $R^7$, $R^8$ are H; $R^5$ is $CH_3$, $R^1$ and $R^2$ are, independently of one another, five- to eight-membered cycloalkyl or heterocycloalkyl, optionally unsaturated one or more times, or are aryl and heteroaryl consisting of one or two rings with a ring size of 5 to 7 members. Said cycles can optionally be substituted by halogen, nitro, amino or alkyl-substituted amino, alkoxy, OH, SH, O and S. The heterocycles mentioned can comprise one or more heteroatoms, in particular N, O or S. It is also possible for $R^1$ and $R^4$ to be $C_2$–$C_8$-alkylene which can optionally be interrupted by one to three, preferably one, 5–7-membered saturated, or unsaturated one or more times, cycles, heterocycles, and aryls or heteroaryls, and the heteroatoms in these cases may be oxygen, sulfur, nitrogen or $R^9$-substituted nitrogen.

Compounds of the formula 1 in which $R^2$, $R^3$, $R^6$, $R^7$, $R^8$ are H, $R^5$ is $CH_3$ are depicted in particular in the following table.

| Compound | $R^1$ | $R^4$ |
| --- | --- | --- |
| 1 | trans | cis/trans |
| 2 | trans | cis/trans |
| 3 | trans | trans |
| 4 | trans | cis |
| 5 | trans | cis/trans |
| 6 | trans | trans |
| 7 | trans | trans |

-continued
| Compound | R¹ | R⁴ |
|---|---|---|
| 8 | 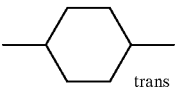 trans | 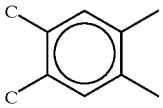 |
| 9 | 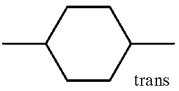 trans | 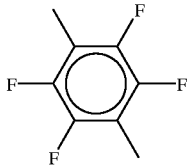 |
| 10 | 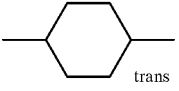 trans | 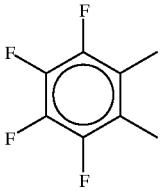 |
| 11 | 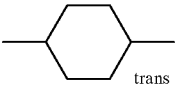 trans | 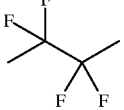 |
| 12 | 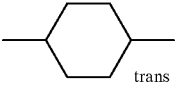 trans | 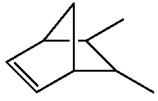 |
| 13 | 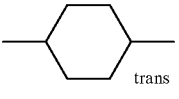 trans | 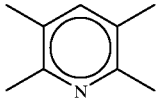 |
| 14 | 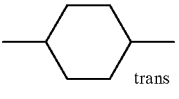 trans | 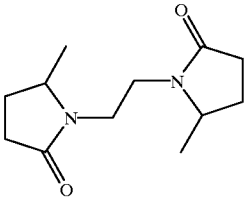 |
| 15 |  trans |  |
| 16 |  trans | 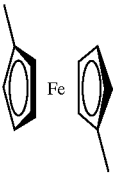 |

-continued
| Compound | R¹ | R⁴ |
|---|---|---|
| 17 |  trans | 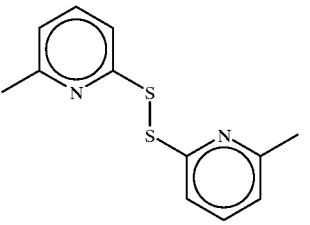 |
| 18 |  trans | 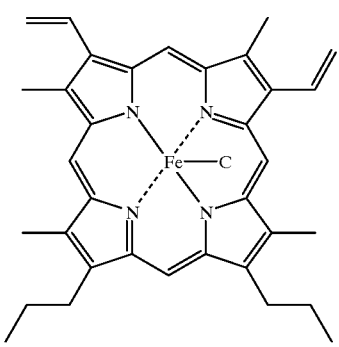 |
| 19 | 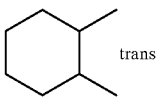 trans |  trans |
| 20 | 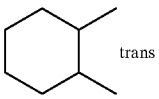 trans |  |
| 21 | 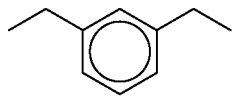 |  |
| 22 | 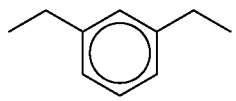 | 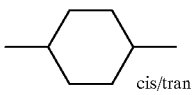 cis/trans |
| 23 | 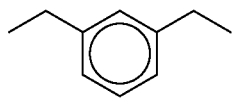 |  |
| 24 | 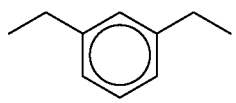 | 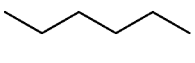 |
| 25 | 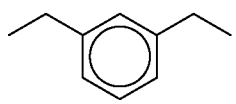 |  trans |

-continued
| Compound | R¹ | R⁴ |
|---|---|---|
| 26 | 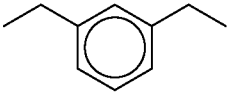 | 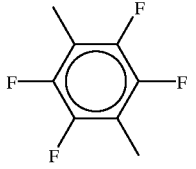 |
| 27 | 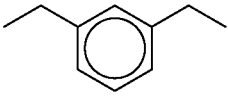 | 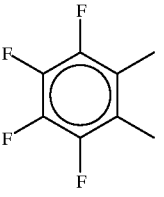 |
| 28 | 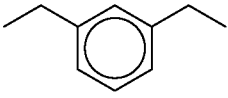 | 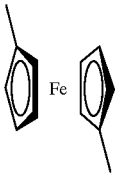 |
| 29 | 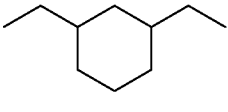 |  |
| 30 | 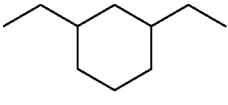 | 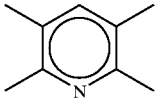 |
| 31 | 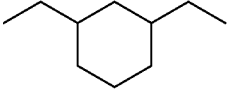 | 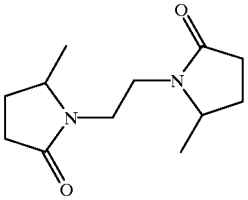 |
| 32 | 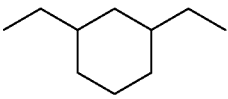 | 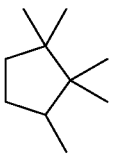 |
| 33 | 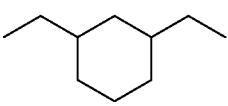 | 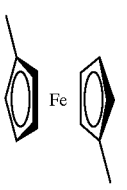 |

-continued
| Compound | R¹ | R⁴ |
|---|---|---|
| 34 | 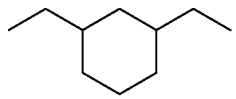 | 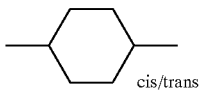 cis/trans |
| 35 | 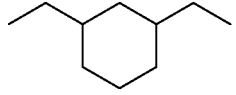 |  |
| 36 | 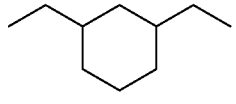 | 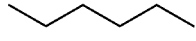 |
| 37 | 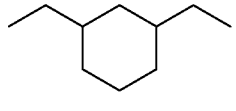 |  |
| 38 | 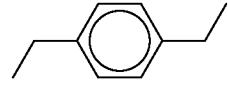 | 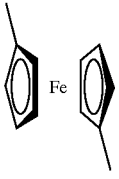 |
| 39 | 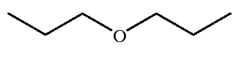 | 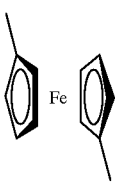 |
| 40 | 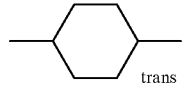 trans | 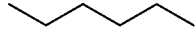 |
| 41 | 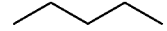 | 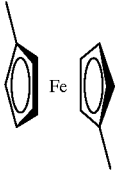 |
| 42 |  |  |

-continued

| Compound | R¹ | R⁴ |
|---|---|---|
| 43 | (heptyl chain) | methyl-ferrocenyl-methyl |
| 44  a = 4 | piperazine with butyl and propyl | cyclohexyl-1,4-dimethyl (cis/trans) |
| 45  a = 4 | piperazine with butyl and propyl | pentyl |
| 46  a = 4 | piperazine with butyl and propyl | 1,4-dimethylphenyl |
| 47  a = 4 | piperazine with butyl and propyl | methyl-ferrocenyl-methyl |
| 48  a = 4 | piperazine with butyl and propyl | propyl |
| 49  a = 4 | homopiperazine with butyl and propyl | methyl-ferrocenyl-methyl |

The meanings applying in the foregoing description are as follows:

alkyl/ene is (also in composite meanings such as alkoxy, alkoxycarbonyl, etc.) in particular $C_1$–$C_5$-alkyl/ene, and $C_1$–$C_5$-alkyl/ene which is substituted by —CN, —$NO_2$, dialkylamine, halogen, OH, SH, —O-alkyl (alkoxy), —$CONH_2$ or alkoxycarbonyl, optionally unsaturated one or more times.

Cycloalkyl/ene is, in particular, $C_3$–$C_8$-cycloalkyl/ene, and cycloalkyl/ene which is substituted by CN, $NO_2$, dialkylamine, halogen, OH, SH, alkoxy, $CONH_2$ or alkoxycarbonyl, optionally unsaturated one or more times.

Aryl/ene is, for example, a five- o r six-membered aromatic system, mainly cyclopentadienide, phenyl/ene or halogen-, OH—, SH—, alkoxy-, $NO_2$—, CN— or alkyl-substituted phenyl/ene.

Heteroaryl/ene is, for example, a six-membered aromatic system which comprises one to three nitrogen atoms or a five-membered aromatic system which comprises one nitrogen, oxygen or sulfur atom, optionally substituted by halogen, OH, SH, alkoxy, $NO_2$, CN or alkyl.

Aryl/ene and heteroaryl/ene are also polyaromatic or fused aromatic systems consisting of 2–8 five- to seven-membered rings, optionally substituted by halogen, OH, SH, alkoxy, $NO_2$, CN or alkyl.

Heterocycloalkyl/ene is, for example, 3–8-membered cycloalkyl/ene which comprises nitrogen, oxygen or sulfur as heteroatom, but is also a polycyclic ring system consisting of 2–4 rings which comprises at least one heteroatom from the group of nitrogen, oxygen or sulfur, optionally substituted by halogen, OH, SH, alkoxy, $NO_2$, CN or alkyl.

Acyl is, for example, $C_{1-5}$-alkanoyl which is optionally substituted by halogen, alkyl, cycloalkyl or aryl. Acyl is preferably acetate and trifluoroacetate.

Halogen is the residue of a hydrohalic acid and is, in particular, fluorine, chlorine, bromine or iodine.

Alkanoyloxy is, in particular, the radical of an optionally halogen-, OH—, SH-substituted $C_{1-5}$-alkanoic acid, in particular $CH_3COO$ and $CF_3COO$.

The radicals R on asymmetric centers in compounds of the formula 1 may be in the α or β position. Accordingly, the invention encompasses both the pure diastereomers and the corresponding mixtures of diastereomers.

The compounds of the invention are prepared, for example, by, in a manner known per se, a) linking a diamine in a suitable solvent such as, for example, $CH_2Cl_2$ to the solid phase such as, for example, chlorotrityl-resin, in the presence of a base such as, for example, diethylisopropylamine;

b) coupling a dicarboxylic acid or a dicarboxylic anhydride to the amine described under a), in a suitable solvent, such as, for example, a $CH_2Cl_2$/N-methylpyrrolidone (NMP) mixture (1:1), in the presence of suitable coupling reagents such as, for example, hydroxybenzotriazole (HOBt) and diisopropylcarbodiimide (DIC);

c) coupling a suitable ergoline derivative such as, for example, 8β-aminomethyl-6-methylergoline, in a suitable solvent such as, for example, NMP, in the presence of suitable coupling reagents such as, for example, HOBt and DIC, to the resin loaded as under b);

d) cleaving the substance prepared under c) off the support material with suitable, acids such as, for example, trifluoroacetic acid (TFA), resulting in compounds of the formula 1 as salts of trifluoroacetic acid;

e) converting the substance obtained as under d) with suitable bases such as, for example, $K_2CO_3$ into the free amine;

f) reacting the derivatives prepared in e) with acids such as, for example, HCl, acetic acid or ammonium salts such as, for example, $NH_4Cl$ and with alkyl and benzyl halides, such as, for example, MeI, $PhCH_2Br$, to give the corresponding ammonium salts, resulting in compounds of the formula 1 as ammonium salts or quaternized amino compounds;

g) reacting the derivatives prepared in e) with acylating agents such as, for example, acetic anhydride, in the presence of basic solvents such as, for example, pyridine, to give the corresponding acylamido derivatives, resulting in compounds of the formula 1 in which $R^2$ is acyl.

The antihypertensive effect was demonstrated in animal experiments with invasive measurement of blood pressure. For this purpose, the substances were administered intravenously and enterally (intraduodenally) to anesthetized rabbits and rats. Dose-dependent falls in blood pressure were observed thereafter, with no adverse effect on the heart rate. There is only an inconsiderable difference in the maximum strength of action after 0.5 mg/kg i.v. or 5 mg/kg i.d., which suggests rapid and complete enteral absorption. The results for selected compounds are compiled in Tables 1 and 2.

The compounds of the formula 1 are suitable on the basis of their antihypertensive activity for use in human medicine as pharmaceuticals for hypertensive diseases or diseases whose symptoms are caused by elevated blood pressure.

The ergoline derivatives of the invention can be used either alone or in combination with other commercially available and novel cardiovascular agents for potentiating the activity of these compounds, which makes it possible to reduce side effects by decreasing the dosages to be employed. The ergoline derivatives can be used either alone or in the form of pharmaceutical products with physiologically tolerated excipients and carriers known from the prior art for said diseases, or conventional pharmacological use forms, such as enteral or parenteral administration, being possible in principle.

The preparation of the ergoline derivatives is to be explained in detail below on the basis of examples, including the findings of the invasive measurement of blood pressure.

1. Substance 1 (9703113): Formula 1 with $R^2$, $R^3$, $R^6$, $R^7$, $R^8$=H; $R^5$=Me; $R^1$=1,4-trans-cyclohexane; $R^4$=1,4-cis/trans-cyclohexane; $C_{34}H_{45}F_6N_5O_6$ (733.76 g/mol);

1.0 g (0.93 mmol/g) of chlorotrityl-resin, 350 mg (3.06 mmol) of trans-1,4-diaminocyclohexane, 2.0 ml of diisopropylethylamine (DIEA), 4.0 ml of $CH_2Cl_2$ are stirred at 25° C. for 6 h. Addition of 0.5 ml of $CH_3OH$ is followed by stirring for a further 30 min. The resin is filtered off and washed 3 times with 3 ml each of $CH_3OH$, $CH_2Cl_2$, i-PrOH, $Et_2O$. It is then reacted in 4 ml of NMP (N-methylpyrrolidone)/$CH_2Cl_2$ (2:1) with 450 mg (2.61 mmol) cis/trans-1,4-cyclohexanedicarboxylic acid, 1.30 g (8.5 mmol) of HOBt and 0.95 ml (6.13 mmol) of DIC at 30° C. for 8 h. It is washed 3 times with 4 ml each of NMP, $CH_2Cl_2$ and $Et_2O$. Addition of 550 mg (2.15 mmol) of 8β-aminomethyl-6-methylergoline in 4 ml of NMP/$CH_2Cl_2$ (1:1) is followed by reaction at 30° C. for 8 h. The resin is then washed 3 times with 3 ml each of NMP, $CH_2Cl_2$, $CH_3OH$, $Et_2O$. The substance is cleaved off with 4 ml of 5% strength trifluoroacetic acid (TFA) in $CH_2Cl_2$. The resin is filtered off and washed twice with 1.5 ml of methanol. The solution is evaporated to dryness in vacuo.

Yield: 252 mg (36.9%), white powder; $[M-2TFA+H]^+$= 507.2 m/e.

Calculated: C, 55.65; H, 6.18; N, 9.54. found: C, 55.00; H, 6.02; N, 9.70%.

2. Substance 2 (9703113.1): Formula 1 with $R^2$, $R^3$, $R^6$, $R^7$, $R^8$=H; $R^5$=Me; $R^1$=1,4-trans-cyclohexane; $R^4$=1,4-cis/trans-cyclohexane; $C_{30}H_{43}N_5O_2$ (505.69 g/mol);

100 mg (0.14 mmol) of substance 1 are stirred in 1.5 ml of $CH_2Cl_2$ with 50 mg of $K_2CO_3$ at 20° C. for 4 h. The filtered solution is evaporated to dryness.

Yield: 65 mg (94.0%), white powder; $[M+H]^+$=507.6 m/e.

3. Substance 3 (9703112): Formula 1 with $R^2$, $R^3$, $R^6$, $R^7$, $R^8$=H; $R^5$=Me; $R^1$=1,4-trans-cyclohexane; $R^4$=p-phenylene; $C_{34}H_{39}F_6N_5O_6$ (727.70 g/mol);

The substance was prepared in analogy to substance 16 using 22 mg (0.13 mmol) of terephthalic acid.

Yield: 12 mg (35.5%), white powder; $[M-2TFA+H]^+$= 501.1 m/e.

4. Substance 4 (9703158): Formula 1 with $R^2$, $R^3$, $R^6$, $R^7$, $R^8$=H; $R^5$=Me; $R^1$=1,4-cyclohexane; $R^4$=cis-1,2-cyclohexane; $C_{34}H_{45}F_6N_5O_6$ (733.76 g/mol);

The substance was prepared in analogy to substance 16 using 20 mg (0.13 mmol) of cis-1,2-cyclohexane-dicarboxylic anhydride.

Yield: 14 mg (41.0%), white powder; [M-2TFA+H]$^+$= 507.5 m/e.

5. Substance 5 (9703159): Formula 1 with $R^2$, $R^3$, $R^6$, $R^7$, $R^8$=H; $R^5$=Me; $R^1$=1,4-cyclohexane; $R^4$=cis/trans-1,3-cyclohexane; $C_{34}H_{45}F_6N_5O_6$ (733.76 g/mol);

The substance was prepared in analogy to substance 16 using 22 mg (0.13 mmol) of cis/trans-1,3-cyclohexane-dicarboxylic acid (mixture of isomers).

Yield: 15 mg (43.9%), colorless, viscous oil; [M-2TFA+H]$^+$=507.4 m/e.

6. Substance 6 (9703152): Formula 1 with $R^2$, $R^3$, $R^6$, $R^7$, $R^8$=H; $R^5$=Me; $R^1$, $R^4$=1,4-trans-cyclohexane; $C_{34}H_{45}F_6N_5O_6$ (733.76 g/mol);

100 mg (0.93 mmol/g) of chlorotrityl-resin, 35 mg (0.31 mmol) of trans-1,4-diaminocyclohexane, 0.5 ml of DIEA, 1.5 ml of $CH_2Cl_2$ are stirred at 25° C. for 6 h. Addition of 0.2 ml of $CH_3OH$ is followed by stirring for a further 30 min. The resin is filtered off and washed 3 times with 1 ml each of $CH_3OH$, $CH_2Cl_2$, i-PrOH, $Et_2O$. It is subsequently reacted in 2 ml of NMP/$CH_2Cl_2$ (2:1) with 45 mg (0.26 mmol) of trans-1,4-cyclohexanedicarboxylic acid, 130 mg (0.85 mmol) of HOBt and 0.1 ml (6.2 mmol) of DIC at 30° C. for 8 h. It is washed 3 times with 1.5 ml each of NMP, $CH_2Cl_2$ and $Et_2O$. Addition of 55 mg (0.21 mmol) of 8β-aminomethyl-6-methylergoline in 2 ml of NMP/$CH_2Cl_2$ (1:1) is followed by reaction at 30° C. for 8 h. The resin is then washed 3 times with 1.5 ml each of NMP, $CH_2Cl_2$, $CH_3OH$, $Et_2O$. The substance is cleaved off with 1 ml of 5% strength TFA in $CH_2Cl_2$. The resin is filtered off and washed twice with 0.5 ml of methanol. The solution is evaporated to dryness in vacuo.

Yield: 43 mg (62.9%), white powder; [M-2TFA+H]$^+$= 507.4 m/e.

7. Substance 7 (9703153): Formula 1 with $R^2$, $R^3$, $R^6$, $R^7$, $R^8$=H; $R^5$=Me; $R^1$=1,4-cyclohexane; $R^4$=trans-1,2-cyclohexane; $C_{34}H_{45}F_6N_5O_6$ (733.76 g/mol);

The substance was prepared in analogy to substance 16 using 22 mg (0.13 mmol) of trans-1,2-cyclohexane-dicarboxylic acid.

Yield: 15 mg (43.9%), white powder; [M-2TFA+H]$^+$= 507.4 m/e.

8. Substance 8 (9703150): Formula 1 with $R^2$, $R^3$, $R^6$, $R^7$, $R^8$=H; $R^8$=Me; $R^1$=trans-1,4-cyclohexane; $R^4$=o-4,5-dichlorophenylene; $C_{34}H_{37}Cl_2F_6N_5O_6$ (796.59 g/mol);

The substance was prepared in analogy to substance 16 using 31 mg (0.13 mmol) of 4,5-dichlorophthalic acid.

Yield: 17 mg (45.9%), white powder; [M-2TFA+H]$^+$= 570.2 m/e.

9. Substance 9 (9703154): Formula 1 with $R^2$, $R^3$, $R^6$, $R^7$, $R^8$=H; $R^5$=Me; $R^1$=trans-1,4-cyclohexane; $R^4$=2,3,5,6-tetrafluoro-p-phenylene; $C_{34}H_{35}F_{10}N_5O_6$ (799.7 g/mol);

The substance was prepared in analogy to substance 16 using 31 mg (0.13 mmol) of 2,3,5,6-tetrafluoro-terephthalic acid.

Yield: 14 mg (37.6%), white powder; [M-2TFA+H]$^+$= 573.1 m/e.

10. Substance 10 (9703156): Formula 1 with $R^2$, $R^3$, $R^6$, $R^7$, $R^8$=H; $R^5$=Me; $R^1$=trans-1,4-cyclohexane; $R^4$=3,4,5,6-tetrafluoro-o-phenylene; $C_{34}H_{35}F_{10}N_5O_6$ (799.7 g/mol);

The substance was prepared in analogy to substance 16 using 31 mg (0.13 mmol) of 3,4,5,6-tetrafluorophthalic acid.

Yield: 12 mg (32.3%), white powder; [M-2TFA+H]$^{1+}$= 573.2 m/e.

11. Substance 11 (9703157): Formula 1 with $R^2$, $R^3$, $R^6$, $R^7$, $R^8$=H; $R^5$=Me; $R^1$=trans-1,4-cyclohexane; $R^4$=1,2-tetrafluoroethylene; $C_{30}H_{35}F_{10}N_5O_6$ (751.6 g/mol);

The substance was prepared in analogy to substance 16 using 25 mg (0.13 mmol) of tetrafluorosuccinic acid.

Yield: 16 mg (45.8%), white powder; [M-2TFA+H]$^+$= 525.1 m/e.

12. Substance 12 (9703136): Formula 1 with $R^2$, $R^3$, $R^6$, $R^7$, $R^8$=H; $R^5$=Me; $R^1$=1,4-cyclohexane; $R^4$=2,3-cis-norbornene; $C_{35}H_{43}F_6N_3O_6$ (743.75 g/mol);

The substance was prepared in analogy to substance 16 using 24 mg (0.13 mmol) of cis-5-norbornene-endo-2,3-dicarboxylic acid.

Yield: 15 mg (43.4%), white powder; [M-2TFA+H]$^+$= 517.8 m/e.

13. Substance 13 (9703137): Formula 1 with $R^2$, $R^3$, $R^6$, $R^7$, $R^8$=H; $R^5$=Me; $R^1$=1,4-cyclohexane; $R^4$=3,5-(2,6-dimethylpyridine); $C_{35}H_{42}F_6N_6O_6$ (756.75 g/mol);

The substance was prepared in analogy to substance 16 using 26 mg (0.13 mmol) of 2,6-dimethylpyridine-3,5-dicarboxylic acid.

Yield: 15 mg (42.6%), white powder; [M-2TFA+H]$^+$= 530.3 m/e.

14. Substance 14 (9703134): Formula 1 with $R^2$, $R^3$, $R^6$, $R^7$, $R^8$=H; $R^5$=Me; $R^1$=1,4-cyclohexane; $R^4$=3,3'-[1,2-bis(5-oxopyrrolidino)ethane]; $C_{36}H_{49}F_6N_7O_8$ (845.84 g/mol);

The substance was prepared in analogy to substance 16 using 37 mg (0.13 mmol) of 1,1'-ethylenebis(5-oxopyrrolidine-3-carboxylic acid.

Yield: 15 mg (38.1%), yellowish oil; [M-2TFA+H]$^+$= 619.7 m/e.

15. Substance 15 (9703135): Formula 1 with $R^2$, $R^3$, $R^6$, $R^7$, $R^8$=H; $R^5$=Me; $R^1$=1,4-cyclohexane; $R^4$=1R,3S-(+)-1'-methyl-2,2'-dimethylcyclopentane; $C_{36}H_{49}F_6N_5O_6$ (761.81 g/mol);

The substance was prepared in analogy to substance 16 using 26 mg (0.13 mmol) of (1R,3S)-(+)-camphoric acid.

Yield: 17 mg (48.0%), white powder; [M-2TFA+H]$^+$= 535.4 m/e.

16. Substance 16 (9703106): Formula 1 with $R^2$, $R^3$, $R^6$, $R^7$, $R^8$=H; $R^5$=Me; $R^1$=4-trans-cyclohexane; $R^4$=1,1'-ferrocene; $C_{38}H_{43}FeF_6N_5O_6$ (835.62 g/mol);

50 mg (0.93 mmol/g) of chlorotrityl-resin, 17.5 mg (0.15 mmol) of trans-1,4-diaminocyclohexane, 0.3 ml of DIEA, 1.0 ml of $CH_2Cl_2$ are stirred at 25° C. for 6 h. Addition of 0.2 ml of $CH_3OH$ is followed by stirring for a further 30 min. The resin is filtered off and washed 3 times with 1 ml each of $CH_3OH$, $CH_2Cl_2$, i-PrOH, $Et_2O$. It is then reacted in 1.5 ml of NMP/$CH_2Cl_2$ (2:1) with 36 mg (0.13 mmol) of 1,1'-ferrocenedicarboxylic acid, 70 mg (0.46 mmol) of HOBt and 50 μl (3.2 mmol) of DIC at 30° C. for 8 h. It is washed 3 times with 2 ml each of NMP, $CH_2Cl_2$ and $Et_2O$. Addition of 30 mg (0.12 mmol) of 8β-aminomethyl-6-methylergoline in 2 ml of NMP/$CH_2Cl_2$ (1:1) is followed by reaction at 30° C. for 8 h. The resin is then washed 3 times with 1.0 ml each of NMP, $CH_2Cl_2$, $CH_3OH$, $Et_2O$. The substance is cleaved off with 0.5 ml of 5% strength TFA in $CH_2Cl_2$. The resin is filtered off and washed twice with 0.2 ml of methanol. The solution is evaporated to dryness in vacuo.

Yield: 17 mg (43.7%), yellowish brown viscous oil; [M-2TFA+H]$^+$=609.8 m/e.

17. Substance 17 (9703155): Formula 1 with $R^2$, $R^3$, $R^6$, $R^7$, $R^8$=H; $R^8$=Me; $R^5$=trans-1,4-cyclohexane; $R^4$=6,6'-dithiodinicotine; $C_{36}H_{41}F_6N_7O_6S_2$ (869.9 g/mol);

The substance was prepared in analogy to substance 16 using 40 mg (0.13 mmol) of 6,6'-dithiodinicotinic acid.

Yield: 16 mg (39.6%), pale brown powder; [M-2TFA+H]$^+$=642.5 m/e.

18. Substance 18 (9703118): Formula 1 with $R^2$, $R^3$, $R^6$, $R^7$, $R^8$=H; $R^5$=Me; $R^1$=1,4-trans-cyclohexane; $R^4$=hemin; $C_{60}H_{65}ClFeF_6N_9O_6$ (1 213.56 g/mol);

The substance was prepared in analogy to substance 16 using 85 mg (0.13 mmol) of hemin.

Yield: 18 mg (31.9%), black powder; [M-Cl]$^+$=952.3 m/e.

19. Substance 19 (9703163): Formula 1 with $R^2$, $R^3$, $R^6$, $R^7$, $R^8$=H; $R^5$=Me; $R^1$=trans-1,2-cyclohexane; $R^4$=cic/trans-1,4-cyclohexane; $C_{34}H_{45}F_6N_5O_6$ (733.76 g/mol);

The substance was prepared in analogy to substance 16 using 18 mg (0.15 mmol) of trans-1,2-cyclohexanediamine and 23 mg (0.13 mmol) of cic/trans-1,4-cyclohexanedicarboxylic acid.

Yield: 14 mg (41.0%), white powder; [M-2TFA+H]$^+$=507.6 m/e.

20. Substance 20 (9703164): Formula 1 with $R^2$, $R^3$, $R^6$, $R^7$, $R^8$=H; $R^5$=Me; $R^1$=trans-1,2-cyclohexane; $R^4$=1,4-phenylene; $C_{34}H_{39}F_6N_5O_6$ (727.70 g/mol);

The substance was prepared in analogy to substance 16 using 17.5 mg (0.15 mmol) of trans-1,2-cyclohexanediamine and 22 mg (0.13 mmol) of terephthalic acid.

Yield: 12 mg (35.5%), white powder; [M-2TFA+H]$^+$=501.1 m/e.

21. Substance 21 (9703126): Formula 1 with $R^2$, $R^3$, $R^6$, $R^7$, $R^8$=H; $R^5$=Me; $R^1$=1,3-bismethylenephenyl; $R^4$=p-phenylene; $C_{36}H_{37}F_6N_5O_6$ (749.71 g/mol);

The substance was prepared in analogy to substance 16 using 21 mg (0.15 mmol) of 3-(aminomethyl)benzylamine and 22 mg (0.13 mmol) of terephthalic acid.

Yield: 16 mg (45.9%), white powder; [M-2TFA+H]$^+$=523.1 m/e.

22. Substance 22 (9703166): Formula 1 with $R^2$, $R^3$, $R^6$, $R^7$, $R^8$=H; $R^5$=Me; $R^1$=1,3-bismethylenephenyl; $R^4$=cic/trans-1,4-cyclohexane; $C_{36}H_{49}N_5O_6$ (647.82 g/mol);

The substance was prepared in analogy to substance 16 using 21 mg (0.15 mmol) of 3-(aminomethyl)benzylamine and 23 mg (0.13 mmol) of cic/trans-1,4-cyclohexanedicarboxylic acid (mixture of isomers). Cleaving off from the resin took place with concentrated acetic acid.

Yield: 15 mg (49.8%), white powder; [M-2TFA+H]$^+$=529.1 m/e.

23. Substance 23 (9703120): Formula 1 with $R^2$, $R^3$, $R^6$, $R^7$, $R^8$=H; $R^5$=Me; $R^1$=1,3-bismethylenephenyl; $R^4$=ethylene; $C_{32}H_{37}N_5O_6$ (701.7 g/mol);

The substance was prepared in analogy to substance 16 using 21 mg (0.15 mmol) of 3-(aminomethyl)benzylamine and 15 mg (0.13 mmol) of succinic acid.

Yield: 12 mg (36.8%), white powder; [M-2TFA+H]$^+$=30 475.3 m/e.

24. Substance 24 (9703123): Formula 1 with $R^2$, $R^3$, $R^6$, $R^7$, $R^8$=H; $R^5$=Me; $R^1$=1,3-bismethylenephenyl; $R^4$=butylene; $C_{34}H_{41}F_6N_5O_6$ (729.72 g/mol);

The substance was prepared in analogy to substance 16 using 21 mg (0.15 mmol) of 3-(aminomethyl)benzylamine and 19 mg (0.13 mmol) of adipic acid.

Yield: 15 mg (44.2%), white powder; [M-2TFA+H]$^+$=503.0 m/e.

25. Substance 25 (9703131): Formula 1 with $R^2$, $R^3$, $R^6$, $R^7$, $R^8$=H; $R^5$=Me; $R^1$=1,3-bismethylenephenyl; $R^4$=cic/trans-1,4-cyclohexane; $C_{36}H_{43}F_6N_5O_6$ (755.76 g/mol);

The substance was prepared in analogy to substance 16 using 21 mg (0.15 mmol) of 3-(aminomethyl)benzylamine and 23 mg (0.13 mmol) of cic/trans-1,4-cyclohexanedicarboxylic acid (mixture of isomers).

Yield: 15 mg (42.7%), white powder; [M-2TFA+H]$^+$=529.2 m/e.

26. Substance 26 (9703161): Formula 1 with $R^2$, $R^3$, $R^6$, $R^7$, $R^8$=H; $R^5$=Me; $R^1$=1,3-bismethylenephenyl; $R^4$=2,3,5,6-tetrafluoro-p-phenylene; $C_{36}H_{33}F_{10}N_5O_6$ (820.58 g/mol);

The substance was prepared in analogy to substance 16 using 21 mg (0.15 mmol) of 3-(aminomethyl)benzylamine and 31 mg (0.13 mmol) of 2,3,5,6-tetrafluoro-terephthalic acid.

Yield: 15 mg (39.3%), gray powder; [M-2TFA+H]$^+$=593.8 m/e.

27. Substance 27 (9703162): Formula 1 with $R^2$, $R^3$, $R^6$, $R^7$, $R^8$=H; $R^5$=Me; $R^1$=1,3-bismethylenephenyl; $R^4$=3,4,5,6-tetrafluoro-o-phenylene; $C_{36}H_{33}F_{10}N_5O6$ (820.58 g/mol);

The substance was prepared in analogy to substance 16 using 21 mg (0.15 mmol) of 3-(aminomethyl)benzylamine and 31 mg (0.13 mmol) of 3,4,5,6-tetrafluorophthalic acid.

Yield: 16 mg (41.9%), gray powder; [M-2TFA+H]$^+$=593.8 m/e.

28. Substance 28 (9703129): Formula 1 with $R^2$, $R^3$, $R^6$, $R^7$, $R^8$=H; $R^5$=Me; $R^1$=1,3-bismethylenephenyl; $R^4$=1,1'-ferrocene; $C_{40}H_{41}FeF_6N_5O_6$ (857.64 g/mol);

The substance was prepared in analogy to substance 16 using 21 mg (0.15 mmol) of 3-(aminomethyl)benzylamine and 36 mg (0.13 mmol) of 1,1'-ferrocenedicarboxylic acid.

Yield: 20 mg (50.1%), yellowish powder; [M-2TFA+H]$^+$=631.7 m/e.

29. Substance 29 (9703140): Formula 1 with $R^2$, $R^3$, $R^6$, $R^7$, $R^8$=H; $R^5$=Me; $R^1$=1,3-bismethylenecyclohexane; $R^4$=2,3-cis-norbornene; $C_{37}H_{47}F_6N_5O_6$ (771.80 g/mol);

The substance was prepared in analogy to substance 16 using 28 mg (0.20 mmol) of 1,3-bis(aminomethyl)cyclohexane and 24 mg (0.13 mmol) of cis-5-norbornene-endo-2,3-dicarboxylic acid.

Yield: 17 mg (47.4%), colorless powder; [M-2TFA+H]$^+$=545.7 m/e.

30. Substance 30 (9703141): Formula 1 with $R^2$, $R^3$, $R^6$, $R^7$, $R^8$=H; $R^5$=Me; $R^1$=1,3-bismethylenecyclohexane; $R^4$=3,5-(2,6-dimethylpyridine); $C_{37}H_{46}F_6N_6O_6$ (784.79 g/mol);

The substance was prepared in analogy to substance 16 using 28 mg (0.20 mmol) of 1,3-bis(aminomethyl)cyclohexane and 26 mg (0.13 mmol) of 2,6-dimethylpyridine-3,5-dicarboxylic acid.

Yield: 12 mg (32.9%), colorless powder; [M-2TFA+H]$^+$=558.6 m/e.

31. Substance 31 (9703138): Formula 1 with $R^2$, $R^3$, $R^6$, $R^7$, $R^8$=H; $R^5$=Me; $R^1$=1,3-bismethylenecyclohexane]; $R^4$=3,3'-[1,2-bis(5-oxopyrrolidino)ethane]; $C_{40}H_{53}F_6N_7O_8$ (873.90 g/mol);

The substance was prepared in analogy to substance 16 using 28 mg (0.20 mmol) of 1,3-bis(aminomethyl)cyclohexane and 37 mg (0.13 mmol) of 1,1'-ethylenebis(5-oxopyrrolidine-3-carboxylic acid).

Yield: 13 mg (32.0%), colorless viscous oil; [M-2TFA+H]$^+$=648.1 m/e.

32. Substance 32 (9703139): Formula 1 with $R^2$, $R^3$, $R^6$, $R^7$, $R^8$=H; $R^5$=Me; $R^1$=1,3-bismethylenecyclohexane; $R^4$=1R,3S-(+)-1'-methyl-2,2'-dimethylcyclopentane; $C_{38}H_{53}F_6N_5O_6$ (789.86 g/mol);

The substance was prepared in analogy to substance 16 using 28 mg (0.20 mmol) of 1,3-bis(aminomethyl)cyclohexane and 26 mg (0.13 mmol) of (1R,3S)-(+)-camphoric acid.

Yield: 12 mg (32.7%), colorless viscous oil; [M-2TFA+H]$^+$=563.7 m/e.

33. Substance 33 (9703130): Formula 1 with $R^2, R^3, R^6, R^7, R^8$=H; $R^5$=Me; $R^1$=1,3-bis-methylenecyclohexane; $R^4$=1,1'-ferrocene; $C_{40}H_{47}FeF_6N_5O_6$ (863.7 g/mol);

The substance was prepared in analogy to substance 16 using 22 mg (0.15 mmol) of 1,3-bisaminomethylcyclohexane (mixture of isomers).

Yield: 15 mg (37.4%), white powder; $[M-2TFA+H]^+$=637.3 m/e.

34. Substance 34 (9703132): Formula 1 with $R^2, R^3, R^6, R^7, R^8$=H; $R^5$=Me; $R^1$=1,3-bismethylenecyclohexane; $R^4$=1,4-cic/trans-cyclohexane; $C_{36}H_{49}F_6N_5O_6$ (761.82 g/mol);

The substance was prepared in analogy to substance 16 using 22 mg (0.15 mmol) of 1,3-bisaminomethylcyclohexane (mixture of isomers) and 22 mg (0.13 mmol) of cis/trans-1,4-cyclohexanedicarboxylic acid.

Yield: 15 mg (42.3%), white powder; $[M-2TFA+H]^+$=535.4 m/e.

35. Substance 35 (9703121): Formula 1 with $R^2, R^3, R^6, R^7, R^8$=H; $R^8$=Me; $R^1$=1,3-bismethylenecyclohexane; $R^4$=ethylene; $C_{32}H_{43}F_6N_5O_6$ (707.7 g/mol);

The substance was prepared in analogy to substance 16 using 22 mg (0.15 mmol) of 1,3-bisaminomethylcyclohexane (mixture of isomers) and 15 mg (0.13 mmol) of succinic acid.

Yield: 13 mg (42.5%), white powder; $[M-2TFA+H]^+$=481.0 m/e.

36. Substance 36 (9703124): Formula 1 with $R^2, R^3, R^6, R^7, R^8$=H; $R^5$=Me; $R^1$=1,3-bismethylenecyclohexane; $R^4$=1,4-butylene; $C_{34}H_{47}F_6N_5O_6$ (735.77 g/mol);

The substance was prepared in analogy to substance 16 using 22 mg (0.15 mmol) of 1,3-bisaminomethylcyclohexane (mixture of isomers) and 19 mg (0.13 mmol) of adipic acid.

Yield: 14 mg (40.9%), white powder; $[M-2TFA+H]^+$=509.2 m/e.

37. Substance 37 (9703127): Formula 1 with $R^2, R^3, R^6, R^7, R^8$=H; $R^5$=Me; $R^1$=1,3-bismethylenecyclohexane; $R^4$=p-phenylene; $C_{36}H_{43}F_6N_5O_6$ (755.8 g/mol);

The substance was prepared in analogy to substance 16 using 22 mg (0.15 mmol) of 1,3-bisaminomethylcyclohexane (mixture of isomers) and 22 mg (0.13 mmol) of terephthalic acid.

Yield: 16 mg (45.5%), white powder; $[M-2TFA+H]^+$=529.2 m/e.

38. Substance 38 (9703144): Formula 1 with $R^2, R^3, R^6, R^7, R^8$=H; $R^5$=Me; $R^1$=1,3-bismethylenephenyl; $R^4$=1,1'-ferrocene; $C_{40}H_{41}FeF_6N_5O_6$ (857.64 g/mol);

The substance was prepared in analogy to substance 16 using 21 mg (0.15 mmol) of 4-(aminomethyl)benzylamine and 36 mg (0.13 mmol) of 1,1'-ferrocenedicarboxylic acid.

Yield: 15 mg (37.6%), yellowish brown powder; $[M-2TFA+H]^+$=631.7 m/e.

39. Substance 39 (9703143): Formula 1 with $R^2, R^3, R^6, R^7, R^8$=H; $R^5$=Me; $R^1$=3-oxo-1,5-pentylene; $R^4$=1,1'-ferrocene; $C_{36}H_{41}FeF_6N_5O_7$ (825.60 g/mol);

The substance was prepared in analogy to substance 16 using 15 mg (0.15 mmol) of 1,4-diazacycloheptane and 36 mg (0.13 mmol) of 1,1'-ferrocenedicarboxylic acid.

Yield: 14 mg (36.5%), yellowish brown powder; $[M-2TFA+H]^+$=598.4 m/e.

40. Substance 40 (9703114): Formula 1 with $R^2, R^3, R^6, R^7, R^8$=H; $R^5$=Me; $R^1$=1,4-trans-cyclohexane; $R^4$=1,4-butylene; $C_{32}H_{43}F_6N_5O_6$ (707.71 g/mol);

The substance was prepared in analogy to substance 16 using 19 mg (0.13 mmol) of adipic acid.

Yield: 13 mg (39.5%), white powder; $[M-2TFA+H]^+$=481.2 m/e.

41. Substance 41 (9703147): Formula 1 with $R^2, R^3, R^6, R^7, R^8$=H; $R^5$=Me; $R^1$=1,3-propylene; $R^4$=1,1'-ferrocene; $C_{35}H_{39}FeF_6N_5O_6$ (795.66 g/mol);

The substance was prepared in analogy to substance 16 using 17 μl (0.20 mmol) of 1,3-diaminopropane and 36 mg (0.13 mmol) of 1,1'-ferrocenedicarboxylic acid.

Yield: 12 mg (32.4%), yellowish brown oil; $[M-2TFA+H]^+$=569.0 m/e.

42. Substance 42 (9703148): Formula 1 with $R^2, R^3, R^6, R^7, R^8$=H; $R^5$=Me; $R^1$=1,2-ethylene; $R^4$=1,1'-ferrocene; $C_{34}H_{37}FeF_6N_5O_6$ (781.63 g/mol);

The substance was prepared in analogy to substance 16 using 13.5 μl (0.20 mmol) of ethylenediamine and 36 mg (0.13 mmol) of 1,1'-ferrocenedicarboxylic acid.

Yield: 11 mg (30.3%), yellowish brown oil; $[M-2TFA+H]^+$=555.2 m/e.

43. Substance 43 (9703149): Formula 1 with $R^2, R^3, R^6, R^7, R^8$=H; $R^5$=Me; $R^1$=hexamethylene; $R^4$=1,1'-ferrocene; $C_{38}H_{45}FeF_6N_5O_6$ (837.65 g/mol);

The substance was prepared in analogy to substance 16 using 23 mg (0.20 mmol) of 1,6-diaminohexane and 36 mg (0.13 mmol) of 1,1'-ferrocenedicarboxylic acid.

Yield: 12 mg (30.8%), yellowish brown powder; $[M-2TFA+H]^+$=611.0 m/e.

44. Substance 44 (9703133): Formula 1 with $R^2, R^3, R^6, R^7, R^8$=H; $R^5$=Me; $R^1$=N,N'-bis(3-propylene)piperazine; $R^4$=1,4-cyclohexane; $C_{42}H_{57}F_{12}N_{7l\,O10}$ (1 047.87 g/mol);

The substance was prepared in analogy to substance 16 using 40 mg (0.20 mmol) of 1,4-bis(3-aminopropyl)piperazine and 23 mg (0.13 mmol) of cic/trans-1,4-cyclohexanedicarboxylic acid (mixture of isomers).

Yield: 21 mg (43.1%), colorless viscous oil; $[M-4TFA+H]^+$=593.0 m/e.

45. Substance 45 (9703122): Formula 1 with $R^2, R^3, R^6, R^7, R^8$=H; $R^5$=Me; $R^1$=N,N'-bis(3-propylene)piperazine; $R^4$=1,4-butylene; $C_{40}H_{55}F_{12}N_7O_{10}$ (1 021.90 g/mol);

The substance was prepared in analogy to substance 16 using 40 mg (0.20 mmol) of 1,4-bis(3-aminopropyl)piperazine and 19 mg (0.13 mmol) of adipic acid.

Yield: 16 mg (33.7%), white powder; $[M-4TFA+H]^+$=567.0 m/e.

46. Substance 46 (9703125): Formula 1 with $R^2, R^3, R^6, R^7, R^8$=H; $R^5$=Me; $R^1$=N,N'-bis(3-propylene)piperazine; $R^4$=p-phenylene; $C_{42}H_{51}F_{12}N_7O_{10}$ (1 041.9 g/mol);

The substance was prepared in analogy to substance 16 using 40 mg (0.20 mmol) of 1,4-bis(3-aminopropyl)piperazine and 22 mg (0.13 mmol) of terephthalic acid.

Yield: 22 mg (45.4%), colorless viscous oil; $[M-4TFA+H]^+$=587.1 m/e.

47. Substance 47 (9703128): Formula 1 with $R^2, R^3, R^6, R^7, R^8$=H; $R^5$=Me; $R^1$=N,N'-bis(3-propylene)piperazine; $R^4$=1,1'-ferrocene; $C_{46}H_{55}FeF_{12}N_7O_{10}$ (1 149.8 g/mol);

The substance was prepared in analogy to substance 16 using 40 mg (0.20 mmol) of 1,4-bis(3-aminopropyl)piperazine.

Yield: 21 mg (39.3%), colorless viscous oil; $[M-4TFA+H]^+$=695.3 m/e.

48. Substance 48 (9703119): Formula 1 with $R^2, R^3, R^6, R^7, R^8$=H; $R^5$=Me; $R^1$=N,N'-bis(3-propylene)piperazine; $R^4$=ethylene; $C_{38}H_{51}F_{12}N_7O_{10}$ (993.9 g/mol);

The substance was prepared in analogy to -substance 16 using 40 mg (0.20 mmol) of 1,4-bis(3-aminopropyl)piperazine and 15 mg (0.13 mmol) of succinic acid.

Yield: 15 mg (32.4%), colorless viscous oil; $[M-4TFA+H]^+$=539.3 m/e.

49. Substance 49 (9703142): Formula 1 with $R^2, R^3$ together $CH_2CH_2$; $R^6, R^7, R^8$=H; $R^5$=Me; $R^1$=$CH_2CH_2CH_2$; $R^4$=1,1'-ferrocene; $C_{37}H_{41}FeF_6N_5O_6$ (821.60 g/mol);

The substance was prepared in analogy to substance 16 using 15 mg (0.15 mmol) of 1,4-diazacycloheptane and 36 mg (0.13 mmol) of 1,1'-ferrocenedicarboxylic acid.

Yield: 12 mg (31.4%), yellowish brown oil; [M-2TFA+H]$^+$=595.8 m/e.

50. Testing on rats

Male Wistar rats with a body weight (BW) of 300–450 g were used as experimental animals. The rats are anesthetized immediately before the experiment with 50 mg/kg pentobarbital Na intraperitoneally (i.p.) or 70 mg/kg inactin i.v. PE tubes are tied into the carotid artery and femoral vein.

To maintain the blood pressure and to prevent formation of thrombi in the PE tubes of the blood vessels, each hour 2.5 ml of heparinized 0.9% strength NaCl solution are infused through the femoral vein and 1.2 ml through the carotid artery.

The arterial blood pressure is measured invasively using a PONEMAH hemodynamic analyzer (HSE, March, Germany). Via the tube in the carotid artery, the arterial blood pressure is mechanoelectrically converted in a Statham transducer (ISOTEC), amplified in a Plugsys (DBA module, type 660), digitized in an A/D converter and input into the PC memory over defined time intervals. The values in the memory are then treated with an adapted algorithm in order to establish the blood pressure parameters to be calculated for heart rate, systolic, diastolic and mean blood pressure.

The ergoline derivatives are administered i.v. through the femoral vein as 5 percent EtOH/NaCl (0.9%) solution, 1 ml/kg in a dosage of 0.5 mg/kg test substance.

The results of the testing are shown in Table 1. The table additionally contains data for comparison compounds known from the literature.

51. Intraduodenal testing of 9703113

The experimental animal used was a female rabbit (White New Zealand) with a body weight (BW) of 3.3 kg. The rabbit was anesthetized immediately before the experiment with 100 mg/kg inactin i.v. PE tubes are tied into the carotid artery and femoral vein, and a rigid tube is tied into the duodenum for intraduodenal administration (i.d.).

To maintain the blood pressure and to prevent formation of thrombi in the PE tubes of the blood vessels, each hour 30 ml of heparinized 0.9% strength NaCl solution are infused through the femoral vein and 7 ml through the carotid artery.

The ergoline derivatives are administered i.d. through the duodenal tube as 5 percent EtOH/NaCl (0.9%) solution, 1 ml/kg in a dosage of 0.5 mg/kg test substance.

Result

| Pressure parameter | Systolic (mm Hg) | Diastolic (mm Hg) | Mean (mm Hg) | Heart rate (beats/min) | Time (min) |
|---|---|---|---|---|---|
| Initial | 113 | 99 | 105 | 278 | 0 |
| Minimum | 87 | 75 | 81 | 260 | 170 |
| Reduction (%): | 23 | 24 | 23 | 7 | |
| End of experiment | 102 | 83 | 91 | 300 | |

The maximum reduction in blood pressure compared with the initial value was between 20 and 30%. During the reduction in blood pressure the heart rate was only slightly decreased by comparison with the start of the experiment.

52. Testing of selected substances after blockade of autonomic nerve tracts with Ecolid Ecolid is a ganglionic blocker which competitively blocks the postsynaptic cholinergic (nicotinergic) receptors in the autonomic ganglia. This interrupts neurotransmission in the ganglia in both the para-sympathetic and sympathetic regions of the autonomic nervous system. The consequence thereof is, inter alia, a fall in blood pressure. It is possible in this way to differentiate central and peripheral (i.e. direct points of action on the smooth muscles) effects.

The experimental animals used were male Wistar rats with a BW of 300–450 g. The rats are anesthetized immediately before the experiment with 70 mg/kg inactin i.v. PE tubes are tied into the carotid artery and femoral vein.

To maintain the blood pressure and to prevent formation of thrombi in the PE tubes of the blood vessels, each hour 2.5 ml of heparinized 0.9% strength NaCl solution are infused through the femoral vein and 1.2 ml through the carotid artery.

Before testing the ergoline derivatives, the experimental animals were treated with Ecolid (dose: 0.5 mg/kg, i.v.).

The ergoline derivatives are administered i.v. through the femoral vein as 5 percent EtOH/NaCl (0.9%) solution, 1 ml/kg in a dosage of 0.5 mg/kg test substance.

The results of the testing are shown in Table 2. The time stated in the table corresponds to the period between administration of Ecolid and injection of the test substances.

53. Relaxation investigations on isolated vessels with 9703113

Side branches of the pig pulmonary artery (fresh specimens from the abattoir) were carefully dissected out and the surrounding pulmonary parenchyma and connective tissue were removed. The vessels were cut into rings about 2–3 mm wide and fixed between platinum wires bent in an L-shape in organ baths. The 10 ml organ baths contained Krebs-Henseleit solution as medium, which was equilibrated at 37° C. and through which a mixture of 95% oxygen and 5% carbon dioxide was passed. The fixed vessel rings were preloaded with a tension of 2 g, which was kept constant throughout the experiment.

The contractions and relaxations were measured isometrically using a F30 force sensor (Hugo Sachs Elektronik, March). After the vessel rings had adapted in the organ bath for a time of 60 minutes, the first contraction took place by addition of KCl (45 mM).

After a resting period of 45 minutes in each case (two bath changes), contractions were induced by $PGF_{2\alpha}$ (3 $\mu$M) or phenylephrine (1 $\mu$M) two to three times until the contraction amplitude remained approximately constant. After a contraction plateau had developed, bradykinin (10 nM) was added. In specimens with an intact endothelium there was an 80–100% relaxation of the pre-contracted vessels. After mechanical removal of the endothelium or preincubation with $N^G$-nitro-L-arginine methyl ester (0.2 nM), which inhibits NO synthesis in the endothelial cells, for 15 minutes, the vessels showed no or a greatly diminished reaction with bradykinin.

The substance to be tested was added to the organ bath when the contraction elicited by $PGF_{2\alpha}$ or phenylephrine had reached its maximum. The relaxation was calculated as a percentage of the preceding contraction (=100%).

| Substances: | | |
|---|---|---|
| | $PGF_{2\alpha}$ | prostaglandin $F_{2\alpha}$ (Serva, Heidelberg) |
| | Bradykinin | bradykinin triacetate (Serva, Heidelberg) |
| | Potassium (KCl) | potassium chloride (Roth, Karlsruhe) |
| | $N^G$-nitro-L-arginine methyl ester | L-NAME (Sigma, Deisenhofen) |
| | Phenylephrine | (Serva, Heidelberg) |
| | Prazosin | (Arzneimittelwerk Dresden) |
| | Krebs- | Data in mM: NaCl 118.0, KCl |

-continued

| | |
|---|---|
| Henseleit solution (pH = 7.4) | 4.7, MgSO$_4$(H$_2$O)$_7$ 1.2, NaHCO$_3$ 25, KH$_2$PO$_4$ 1.2, CaCl$_2$, glucose 11. |

The contraction induced by KCl is not reduced by the substance 9703113 (30 μM). Accordingly, it is to be assumed that there is no calcium-antagonistic effect (inhibition of voltage-operated calcium channels) at the concentration tested.

According to the present investigations, the substance 9703113 relaxes in a concentration-dependent manner phenylephrine-precontracted vessels (cf. FIG. 1). The relaxation is endothelium-independent because the relaxation is not significantly altered even on inhibition of NO synthesis by L-NAME. These results indicate that the tested substance mainly elicits relaxation of α$_1$-adrenoceptors because complete inhibition of the contraction induced by phenylephrine is achieved.

Viewed overall, the investigations indicate that the vasodilating and the hypotensive effect of the substance 9703113 are brought about by blockade of α$_1$-adrenoceptors.

The effect of the substance 9703113 on isolated pig pulmonary artery precontracted with phenylephrine is depicted in FIG. 1 which is appended.

TABLE 1.1

Effect of various 8β-aminomethylergoline derivatives of formula 1, and various comparison products, on the arterial blood pressure of normotensive Wistar rats (dose: 0.5 mg/kg, i.v.)

| Assessment Pressure Duration | → no effect to 5% (↓) < 5 min | (↓) to 10% ↓ up to 10 min | ↓ to 20% ↓↓ up to 30 min | ↓↓ to 30% ↓↓↓ >30 min | ↓↓↓ >30% ↓↓↓ >30 min | |
|---|---|---|---|---|---|---|
| Substance | Systol. pressure % | Diastol. pressure % | Mean pressure % | Heart rate beats/min | Duration min | Effect pressure/ duration |
| TFA (equimolar) | 4.3 | 5.1 | 4.6 | → | >1 | (↓)/(↓) |
| Dihydroergocornine | 5.0 | 4.3 | 3.3 | → | 3 | '/(↓) |
| Dihydrolysergamide | 8.0 | 7.1 | 8.0 | → | 5 | (↓)/(↓) |
| 8β-Aminomethyl-6-methylergoline | 16.4 | 14.3 | 15.3 | → | 30 | ↓/↓↓ |
| Minoxidil | 6.6 | 8.1 | 7.1 | → | ca 10 | ↓/↓ |
| Dihydro-1-[[6-methyl-ergolin-8b-yl]-methyl]2,4-(1H, 3H)-pyrimidinedione | 70.9 | 75.9 | 72.3 | → | ca 10 | ↓↓↓/↓ |
| 9703106* | 24.0 | 24.6 | 25.3 | → | 100 | ↓↓↓/↓↓↓ |
| 9703112 | 25.2 | 31.7 | 29.2 | → | 18 | ↓↓↓/↓↓ |
| 9703113 | 31.4 | 40.8 | 29.1 | (↓) | 60 | ↓↓↓/↓↓↓ |
| 9703114 | 18.8 | 20.7 | 20.3 | → | 40 | ↓↓↓/↓↓↓ |
| 9703123 | 38.0 | 44.3 | 43.4 | → | 7 | ↓↓↓/↓ |
| 9703125 | 13.1 | 14.0 | 13.7 | → | 90 | ↓/↓↓↓ |
| 9703126 | 55.0 | 63.0 | 60.0 | → | >60 | ↓↓↓/↓↓↓ |
| 9703127 | 24.8 | 29.0 | 27.2 | → | >25 | ↓↓↓/↓↓ |
| 9703128 | 32.6 | 42.9 | 38.3 | → | 45 | ↓↓↓/↓↓↓ |
| 9703129 | 59.0 | 65.7 | 62.0 | → | >85 | ↓↓↓/↓↓↓ |
| 9703130 | 60.9 | 65.2 | 58.3 | → | ca 60 | ↓↓↓/↓↓↓ |
| 9703131 | 47.5 | 55.2 | 51.6 | → | >240 | ↓↓↓/↓↓↓ |
| 9703133 | 48.4 | 50.0 | 45.4 | ↑ | ca 60 | ↓↓↓/↓↓↓ |
| 9703136 | 34.5 | 31.0 | 35.4 | → | >80 | ↓↓↓/↓↓↓ |
| 9703137 | 56.5 | 64.8 | 60.2 | → | ca 95 | ↓↓↓/↓↓↓ |
| 9703138 | 15.7 | 18.2 | 17.5 | → | 180 | ↓/↓↓↓ |

*1 mg/kg i.v.

TABLE 1.2

Effect of various 8β-aminomethylergoline derivatives of formula 1 on the arterial blood pressure of normotensive Wistar rats (dose: 0.5 mg/kg, i.v.)

| Assessment Pressure Duration | ↓ no effect to 5% | (↓) to 10% (↓) < 5 min | ↓ to 20% ↓ up to 10 min | ↓↓ to 30% ↓↓ up to 30 min | ↓↓↓ > 30% ↓↓↓ > 30 min | |
|---|---|---|---|---|---|---|
| Substance | Systol. Pressure % | Diastol. Pressure % | Mean pressure % | Heart rate beats/ min | Duration min | Effect pressure/ duration |
| 9703140 | 36.1 | 36.7 | 37.1 | → | 20 | ↓↓↓/↓↓ |
| 9703142 | 32.5 | 35.9 | 34.8 | → | 4 | ↓↓↓/(↓) |
| 9703143 | 42.7 | 49.4 | 46..0 | → | 45 | ↓↓↓/↓↓↓ |
| 9703147 | 45.4 | 43.5 | 44.0 | → | 120 | ↓↓↓/↓↓↓ |
| 9703152 | 48.2 | 48.0 | 48.4 | → | >90 | ↓↓↓/↓↓↓ |
| 9703155 | 24.7 | 25.9 | 26.9 | → | ca 60 | ↓↓/↓↓↓ |

TABLE 1.2-continued

Effect of various 8β-aminomethylergoline derivatives of formula 1 on the arterial blood pressure of normotensive Wistar rats (dose: 0.5 mg/kg, i.v.)

Assessment
Pressure: ↓ no effect to 5%    (↓) to 10%    ↓ to 20%    ↓↓ to 30%    ↓↓↓ > 30%
Duration:                       (↓) < 5 min   ↓ up to 10 min   ↓↓ up to 30 min   ↓↓↓ > 30 min

| Substance | Systol. Pressure % | Diastol. Pressure % | Mean pressure % | Heart rate beats/min | Duration min | Effect pressure/duration |
|---|---|---|---|---|---|---|
| 9703156 | 33.4 | 43.4 | 38.6 | → | 13 | ↓↓↓/↓↓ |
| 9703157 | 46.6 | 49.6 | 48.8 | → | 30 | ↓↓↓/↓↓ |

TABLE 2

Effect of various 8β-aminogoline derivatives of formula 1, and of a comparison product, on the arterial blood pressure of normotensive Wistar rats after pretreatment with Ecolid (dose: 0.5 mg/kg, i.v.)

Assessment
Pressure: → no effect to 5%    (↓) to 10%    ↓ to 20%    ↓↓ to 30%    ↓↓↓ > 30%
Duration:                       (↓) < 5 min   ↓ up to 10 min   ↓↓ up to 30 min   ↓↓↓ > 30 min

| Substance | Systol. Pressure % | Diastol. pressure % | Mean pressure % | Heart rate beats/min | Duration min | Effect pressure/duration |
|---|---|---|---|---|---|---|
| Ecolid | 52.6 | 54.7 | 50.4 | → | n.d. | ↓↓↓/↓↓↓ |
| Dihydro-1-[[6-methyl-ergolin 8b-yl]methyl]2,4-(1H, 3H) pyrimidinedione | 0 | 0 | 0 | → | 0 | →/→ |
| 9703113 | 21.8 | 33.4 | 29.9 | → | >120 | ↓↓↓/↓↓↓ |
| 9703131 | 32.9 | 40.4 | 32.4 | → | >60 (exp. stopped) | ↓↓↓/↓↓↓ |
| 9703126 | 36.4 | 48.7 | 43.7 | → | >120 | ↓↓↓/↓↓↓ |

What is claimed is:

1. An aminomethylergoline derivative of formula 1:

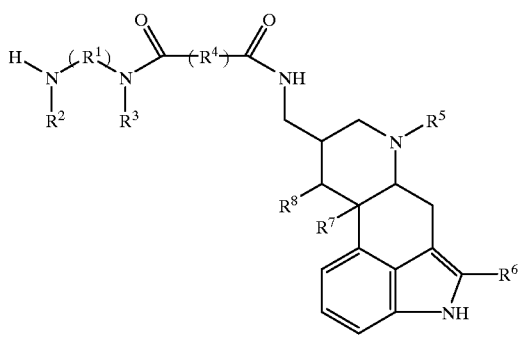

(1)

in which
$R^5$=H, alkyl, aryl, acyl, CN;
$R^6$=H, alkyl, halogen;
$R^7$, $R^8$=H or together a bond;
$R^1$ together with the two adjacent N atoms is the residue of a diamine;
$R^4$ together with the two adjacent carbonyl groups is the residue of a dicarboxylic acid; and
$R^2$ is H, acyl and $R^3$ is H, or $R^2$ and $R^3$ together are a divalent radical $R^1$, and salts thereof.

2. A compound of the formula 1 as claimed in claim 1, in which $R^1$ and $R^4$ have the following meanings:
   a) $R^1$ and $R^4$ are, independently of one another, $C_1$–$C_{10}$-alkylene, branched or unbranched, which is optionally interrupted by O, S, NH, $NR^9$, arylene, heteroarylene, cycloalkylene, heterocycloalkylene and/or optionally substituted by $R^{10}$,
   $R^9$=alkyl, benzyl, aryl, acyl,
   $R^{10}$=$R^9$, also halogen, OH, SH, $NO_2$, CN;
   b) $R^1$ and $R^4$ are, independently of one another, $C_1$–$C_{10}$-alkylene, branched or unbranched, which comprises one or more isolated and conjugated double bonds and is optionally substituted by $R^{10}$, and/or is optionally interrupted by O, S, NH, $NR^9$, arylene, heteroarylene, cycloalkylene, heterocycloalkylene;
   c) $R^1$ and $R^4$ are, independently of one another, cycloalkylene or heterocycloalkylene with 3–8 ring members or such cycles with, optionally, 1–2 bridges with in each case 1–3 chain members, which comprise C, O, NH, $NR^9$, S, and arylene or heteroarylene with 5–7 ring members, which are optionally substituted by $R^{10}$;
   d) $R^1$ and $R^4$ are, independently of one another, two cycloalkylenes linked by $R^{11}$ and optionally interrupted in the ring by O, S, NH, $NR^9$ and/or optionally substituted by $R^{10}$, O or S;
   $R^{11}$=alkylene, O, S, $S_2$, $NR^9$.

3. A compound of the formula 1 as claimed in claim 1, in which

R¹ has one of the following meanings:
  a) R¹ is $C_1$–$C_{10}$-alkylene, branched or unbranched, which is optionally interrupted by O, S, NH, $NR^9$, arylene, heteroarylene, cycloalkylene, heterocycloalkylene and/or optionally substituted by $R^{10}$, wherein
    $R^9$=alkyl, benzyl, aryl, acyl, and
    $R^{10}$=$R^9$, halogen, OH, SH, $NO_2$, or CN;
  b) R¹ is $C_1$–$C_{10}$-alkylene, branched or unbranched, which comprises one or more isolated and conjugated double bonds and is optionally substituted by $R^{10}$, and/or is optionally interrupted by O, S, NH, $NR^9$, arylene, heteroarylene, cycloalkylene, heterocycloalkylene;
  c) R¹ is cycloalkylene or heterocycloalkylene with 3–8 ring members or such cycles with, optionally, 1–2 bridges with in each case 1–3 chain members, which comprise C, O, NH, $NR^9$, S, and arylene or heteroarylene with 5–7 ring members, which are optionally substituted by $R^{10}$; or
  d) R¹ is two cycloalkylenes linked by $R^{11}$ and optionally interrupted in the ring by O, S, NH, $NR^9$ and/or optionally substituted by $R^{10}$, O or S, wherein $R^{11}$= alkylene, O, S, $S_2$, $NR^9$; and
R⁴ has one of the following meanings:
  a) R⁴ is two arylene or heteroarylene radicals linked by $R^{12}$, wherein
    $R^{12}$=alkylene, Fe, O, S, $S_2$, $NR^9$; or
  b) R⁴ is porphyrindiyl, optionally substituted one or more times by alkyl, unsaturated one or more times, having central atoms such as, for example, Zn, Ca, Mg and Fe, where a residual charge occurring after the complexation is neutralized by an anion of a pharmaceutically acceptable acid.

4. A compound of formula 1 as claimed in claim 1, in which
  $R^2$, $R^3$, $R^6$, $R^7$, $R^8$ are H; $R^5$ is $CH_3$,
  R¹ and R² are, independently of one another, five- to eight-membered cycloalkyl or heterocycloalkyl, optionally unsaturated one or more times, or are aryl and heteroaryl consisting of one or two rings with a ring size of 5 to 7 members, where the said cycles are optionally substituted by halogen, nitro, amino or alkyl-substituted amino, alkoxy, OH, SH, O and S, the heterocyclyl radicals comprise one or more heteroatoms selected from N, O or S; or
  R¹ and R⁴ are $C_2$–$C_8$-alkylene which is optionally interrupted by one to three, preferably one, 5–7-membered saturated, or unsaturated one or more times, cycles, heterocycles, and aryls or heteroaryls, where the heteroatoms are selected from the group of O, S, NH or $NR^9$.

5. A compound of the formula 1 as claimed in claim 1, in which $R^2$, $R^3$, $R^6$, $R^7$, $R^8$ are H;
  $R^5$ is $CH_3$, and the radicals R¹ and R⁴ have the following meanings:

| Compound | R¹ | R⁴ |
|---|---|---|
| 1 |  trans | 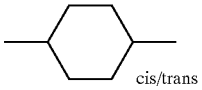 cis/trans |
| 2 | 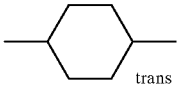 trans | 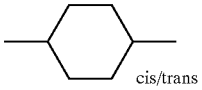 cis/trans |
| 3 |  trans |  |
| 4 |  trans | 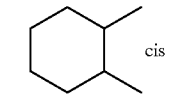 cis |
| 5 | 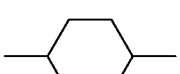 trans | 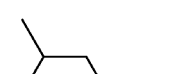 cis/trans |
| 6 | 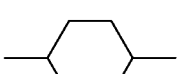 trans | 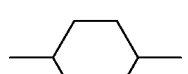 trans |

-continued
| Compound | R¹ | R⁴ |
|---|---|---|
| 7 |  trans | 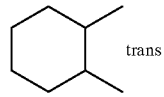 trans |
| 8 |  trans | 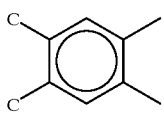 |
| 9 |  trans | 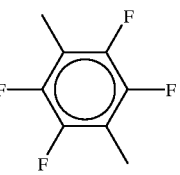 |
| 10 |  trans | 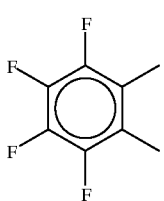 |
| 11 | 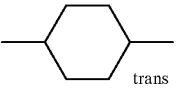 trans | 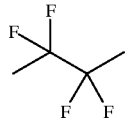 |
| 12 | 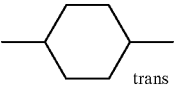 trans | 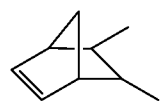 |
| 13 |  trans | 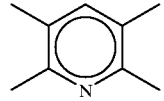 |
| 14 |  trans | 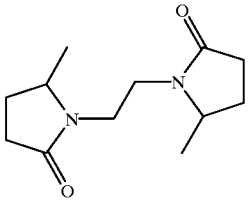 |
| 15 | 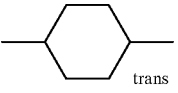 trans |  |

-continued
| Compound | R¹ | R⁴ |
|---|---|---|
| 16 |  trans | 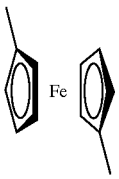 |
| 17 |  trans | 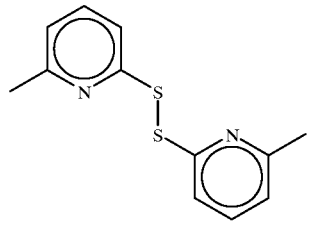 |
| 18 |  trans | 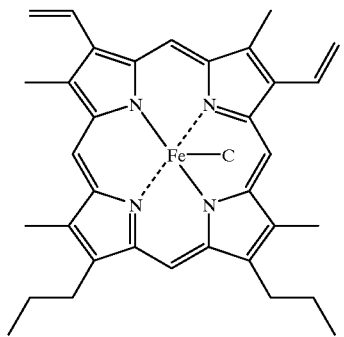 |
| 19 | 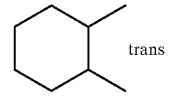 trans | 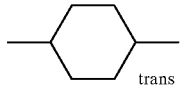 trans |
| 20 | 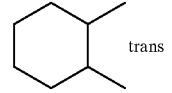 trans | 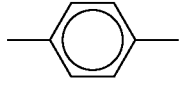 |
| 21 | 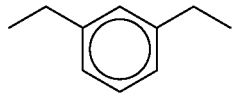 | 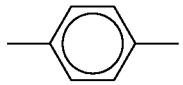 |
| 22 | 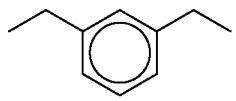 |  cis/trans |
| 23 | 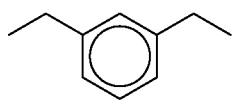 |  |
| 24 | 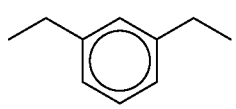 | 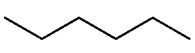 |

-continued

| Compound | R¹ | R⁴ |
|---|---|---|
| 25 | 1,3-diethylbenzene | trans-1,4-dimethylcyclohexane |
| 26 | 1,3-diethylbenzene | 1,2,3,4-tetrafluoro-5,6-dimethylbenzene |
| 27 | 1,3-diethylbenzene | 1,2,3,4-tetrafluoro-5,6-dimethylbenzene |
| 28 | 1,3-diethylbenzene | 1,1'-dimethylferrocene |
| 29 | 1,3-diethylcyclohexane | 2,3-dimethylnorbornene |
| 30 | 1,3-diethylcyclohexane | 2,3,5,6-tetramethylpyridine |
| 31 | 1,3-diethylcyclohexane | 1,1'-(ethane-1,2-diyl)bis(5-methylpyrrolidin-2-one) |
| 32 | 1,3-diethylcyclohexane | 1,1,2,2,3-pentamethylcyclopentane |

-continued
| Compound | R¹ | R⁴ |
|---|---|---|
| 33 | 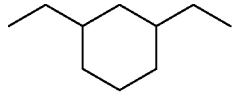 | 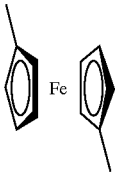 |
| 34 | 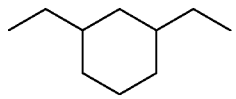 | 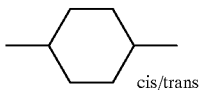 cis/trans |
| 35 | 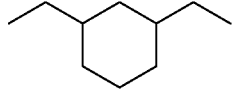 |  |
| 36 | 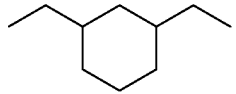 | 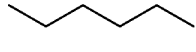 |
| 37 | 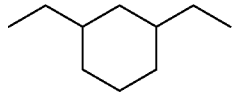 |  |
| 38 | 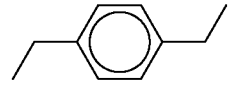 | 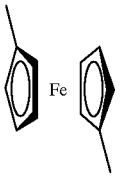 |
| 39 | 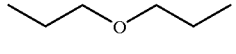 | 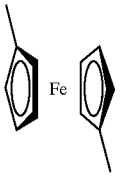 |
| 40 | 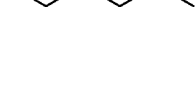 trans |  |
| 41 | 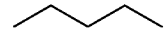 | 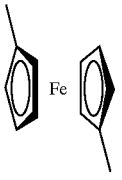 |

-continued
| Compound | R¹ | R⁴ |
|---|---|---|
| 42 |  | 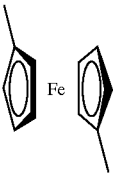 |
| 43 | 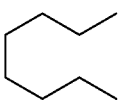 | 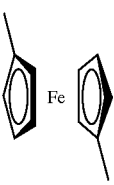 |
| 44 a = 4 | 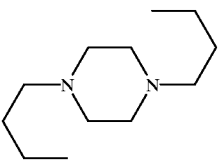 |  cis/trans |
| 45 a = 4 | 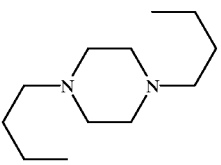 |  |
| 46 a = 4 | 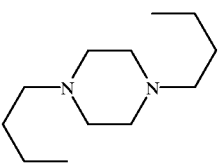 |  |
| 47 a = 4 | 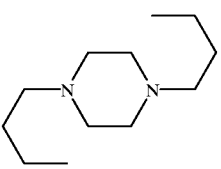 | 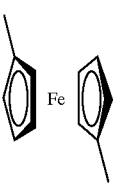 |
| 48 a = 4 | 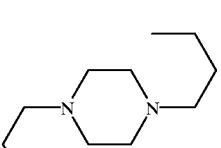 | 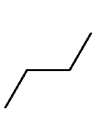 |
| 49 a = 4 | 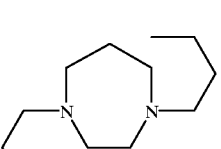 | 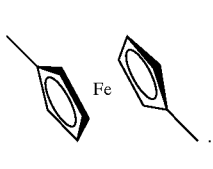 |

6. A pharmaceutically acceptable salt of a compound of the formula 1 as claimed in claim 1.

7. A pharmaceutical composition comprising a compound of the formula 1 as claimed in claim 1 together with conventional excipients and carriers.

8. A pharmaceutical composition as claimed in claim 7, further comprising other commercially available or novel cardiovascular agents.

9. A method of treating hypertensive diseases or diseases whose symptoms are caused by elevated blood pressure in a patient which comprises administering a therapeutically effective amount of a compound of the formula 1 as claimed in claim 1.

10. A method of treating hypertension or high blood pressure in a patient which comprises administering a therapeutically effective amount of a compound of the formula 1 as claimed in claim 1.

* * * * *